United States Patent [19]

Oyama et al.

[11] Patent Number: 4,521,514

[45] Date of Patent: Jun. 4, 1985

[54] PROCESS FOR PRODUCING AN ADDITION COMPOUND OF A DIPEPTIDE ESTER AND AN AMINO ACID ESTER

[75] Inventors: Kiyotaka Oyama, Hikari; Shigeaki Irino, Tokuyama; Tsuneo Harada, Shinnanyo; Masao Nakamura, Yokohama, all of Japan

[73] Assignees: Toyo Soda Manufacturing Co., Ltd., Shinnanyo; Ajinomoto Co., Inc.; Sagami Chemical Research Center, both of Tokyo, all of Japan

[21] Appl. No.: 516,344

[22] Filed: Jul. 22, 1983

[30] Foreign Application Priority Data

Jul. 23, 1982 [JP] Japan ................................ 57-128420

[51] Int. Cl.³ ...................... C12P 21/02; C07C 103/52
[52] U.S. Cl. ................................. 435/70; 260/112.5 R
[58] Field of Search ...................................... 435/70, 68

[56] References Cited

U.S. PATENT DOCUMENTS 4,165,311 8/1979 Isowa et al. ..................... 435/68 X
4,284,721 8/1981 Oyama et al. ........................ 435/70

*Primary Examiner*—Lionel M. Shapiro
*Attorney, Agent, or Firm*—Oblon, Fisher, Spivak, McClelland & Maier

[57] ABSTRACT

A process for producing an addition compound of N-benzyloxycarbonyl-α-L-aspartyl-L-phenylalanine methyl ester and phenylalanine methyl ester. Benzyloxycarbonylation of the amino group of L-aspartic acid by benzyloxycarbonylchloride in the presence of a base and esterification of phenylalanine containing its L-body by methanol in the presence of an acid are carried out and both the reaction solutions are admixed after residual methanol is removed from the esterification reaction solution. A proteolytic enzyme is added to the resulting mixture solution after it is adjusted to have a pH, value, at which no substantial deactivation of the enzyme occurs. The reaction of N-benzyloxycarbonyl-L-aspartic acid and phenylalanine methyl ester is carried out in the solution at a pH, at which the proteolytic enzyme exerts the enzymatic activity to deposit the addition compound which is then recovered.

12 Claims, No Drawings

PROCESS FOR PRODUCING AN ADDITION COMPOUND OF A DIPEPTIDE ESTER AND AN AMINO ACID ESTER

BACKGROUND OF THE INVENTION

1. Field of the Invention

This invention relates to a process for producing an addition compound of a dipeptide ester and an amino acid ester and more particularly to a process for producing an addition compound of N-benzyloxycarbonyl-$\alpha$-L-aspartyl-L-phenylalanine methyl ester and phenylalanine methyl ester from aspartic acid, benzyloxycarbonyl chloride, phenylalanine and methanol, in which an enzymatic reaction is utilized.

2. Description of the Prior Art

It has been known that an addition compound of a dipeptide ester and an amino acid ester is produced by reacting a monoaminodicarboxylic acid, of which amino group is protected, and a monoaminomonocarboxylic acid converted into an ester by protecting its carboxyl group with an lower alkoxyl group, in the presence of a proteotylic enzyme, and further by forming an addition compound of the reaction product and the ester (U.S. Pat. No. 4,165,311).

Thus produced addition compounds are imported materials as intermediates for foods, medicines, pharmaceuticals and the like. Among them, the addition compound of N-benzyloxycarbonyl-$\alpha$-L-aspartyl-L-phenylalanine methyl ester and phenylalanine methyl ester (hereinafter referred to as ZAPM.PM for the abbreviation) is particularly important because it can be easily derived to a low calorie sweetener, "aspartame".

According to the above-stated known process, ZAPM.PM is produced any way from N-benzyloxycarbonylaspartic acid (hereinafter referred to as ZA) or its salt and phenylalanine methyl ester (hereinafter referred to as PM) as starting materials. In such a case, isolated (crystallized) ones of these starting materials which are in highly purified state are used.

It is possible in a reaction using an enzyme to cause the inhibition or deactivation of the enzyme depending on the situation when there are impurities in the reaction system and therefore it is general to carry out the reaction in avoiding their coexistence.

Crystalline ZA is usually obtained in a way in that after aspartic acid and benzyloxycarbonyl chloride are reacted in an aqueous solution in the presence of a base, ZA is crystallized by adding an acid to convert pH of the reaction solution into the acidic side, isolating and drying it. The other starting material, PM (hydrochloric acid salt) is obtained in that after phenylalanine is reacted with methanol in the presence of hydrogen chloride, methanol is removed by distillation to isolate crystalls of hydrochloric acid salt of PM which is then dried.

SUMMARY OF THE INVENTION

An object of this invention is to provide a process for producing an addition compound of ZAPM and PM in which ZA and PM formation steps are organized to couple with subsequent ZAPM.PM production steps.

Another object of this invention is to provide a process for producing the addition compound in reduced steps.

A further object of this invention is to provide a process for producing the addition compound in which loss of the main starting materials, aspartic acid and phenylalanine is suppressed.

A still further object of this invention is to provide a process for producing the addition compound in which consumption of other raw materials are reduced.

Accordingly, this invention provide a process for producing an addition compound of a dipeptide ester and an amino acid ester, in which aspartic acid and benzyloxycarbonyl chloride is reacted in an aqueous solution in the presence of a base to prepare a solution containing N-benzyloxycarbonyl aspartic acid; phenylalanine and methanol are separatedly reacted in the presence of an acid to produce phenylalanine methyl ester; excess methanol is substituted with water to convert it to an aqueous solution of phenylalanine methyl ester; it is admixed with the above-prepared aqueous solution containing N-benzyloxycarbonyl aspartic acid; an proteolytic enzyme is added into the resulting mixture under conditions, under which no substantial deactivation of the enzyme occurrs; N-benzyloxycarbonyl aspartic acid and phenylalanine methyl ester are reacted under conditions, under which the proteolytic enzyme exerts the enzymatic activity, to deposit an addition compound of N-benzyloxycarbonyl-$\alpha$-L-aspartyl-L-phenylalanine methyl ester and phenylalanine methyl ester; and then the addition compound is recovered.

DETAILED DESCRIPTION OF THE INVENTION

Each one of aspartic acid and phenylalanine used in this invention is of L-form or a mixture of L-form and D-form.

The preparation of aqueous ZA solution, which is one of the first step reactions of this invention, can be carried out according to a conventional method such as Schotten-Baumann method of introducing a N-benzyloxycarbonyl group which is a protecting group of an amino group of an amino acid. That is to say, into an aqueous solution containing about 5 to 50% by weight of aspartic acid and 1 to about 3 times amount of a base by molar ratio based on the amount of aspartic acid is added benzyloxycarbonyl chloride in 1 to about 2 times amount by molar ratio based on the amount of aspartic acid, and the base is further added to the resulting mixture in about 1 to about 3 times amount by the same standard, while the temperature of the reaction solution ranges 0° to 30° C. A salt of aspartic acid may be used in place of aspartic acid (and a part of the base). Any one of organic or inorganic base can be used as the basic substance used here except for ammonia and primary and secondary amines. Among them, alkali-metal hydroxides such as sodium hydroxide and potassium hydroxide, and carbonates of alkali metals such as sodium carbonate, potassium carbonate, sodium hydrogen carbonate and potassium hydrogen carbonate can be listed as particularly preferable examples in view of the industrial stand point. The aqueous solution of ZA thus prepared can be served to the next step, but it is desirable to wash it with an organic solvent such as toluene, ethylene dichloride, a petroleum ether, methyl isobutyl ketone and the like which can make up a binary phases with water, because the solution may contain benzyl alcohol, unreacted benzyloxycarbonyl chloride and the like. The aqueous solution containing ZA may be also prepared in that the N-benzyloxycarbonylation reaction is carried out in the presence of these solvents to separate the two phases after the reaction.

The preparation of PM solution, which is another first step reaction of this invention, is a reaction in that phenylalanine and methanol is reacted according to a conventional method such as Fischer method for esterifying an amino acid in methanol in the presence of an acid, followed by the substitution of methanol with water.

As the species of the acid used here, there is no restriction regarding whether inorganic or organic acids. For example, anhydrous hydrogen chloride, hydrogen bromide, sulfuric acid, toluene sulphonic acid can be used but hydrogen chloride and sulfuric acid are particularly preferable in view of the industrial stand point. The esterification generally carried out in methanol in the presence of the acid at least in an equivalent amount based on the amount of phenylalanine and generally 1.5 to about 20 times amount by molar ratio, at a temperature which may be within a range from about 0° C. to a reflux temperature. However, if too much amount of acid is used, this produces a large amount of salt when neutralized and therefore tends to cause a deposit of the salt in later steps. Accordingly, the amount is preferably from about 1.5 to about 5 times based on the amount of phenylalanine. Methanol is usually used in an large excess amount based on the amount of phenylalanine. From the reaction mixture, methanol can be replaced with water by means of distillation or the like to remove methanol after the addition of water or simultaneously adding water. It tends to occur the hydrolysis of PM by the acid during the distillation but the hydrolysis can be effectively suppressed by neutralizing the excess of acid with a base before the distillation.

The thus obtained aqueous solution containing PM is admixed with the aqueous ZA solution prepared as above-stated, directly or after concentrating or diluting it with water depending on the concentration of the PM contained. PM may by extracted by a proper organic solvent after the addition of a base to liberate PM into the free form and again extracted after the separation of liquids from the thus resulting organic solvent solution by admixing it with an acidic aqueous solution to contact to give the aqueous PM solution.

The thus obtained aqueous solution containing ZA and aqueous solution containing PM are mixed to give an aqueous solution containing ZA and PM. The ratio of mixing is in a range to effect that the amounts of ZA and PM are in a suitable range in the aqueous solution for the production conditions of ZAPM.PM according to the below-stated enzymatic reaction. It is natural that a supplemental addition of ZA or PM prepared by another method may be allowed so as to secure the range, when it is the case, wherein a ratio slightly deviating from the range is given.

In this invention a proteolytic enzyme is then added into the thus prepared aqueous mixture solution of ZA and PM and conduct the second step reaction, the formation and deposition of ZAPM.PM by the enzymatic reaction. It is necessary to carry out the addition of the proteolytic enzyme in a condition wherein the aqueous mixture solution has a pH value at which no substantial deactivation of the enzyme occurs. However, it is easy to control it to a value of neutral neighborhood because the aqueous solutions of ZA and PM are basic and acidic in nature before the admixing and therefore it takes place a neutralization by the admixing.

As the proteolytic enzyme used in this invention, thiol proteinase, serine proteinase, acidic proteinase and the like can be used but an enzyme having a metal ion in the active center, that is, a metallo-proteinase is the most preferable. As their examples, here can be listed ones originating from microorganisms, for example, proteinanes originating from actinomycetes such as Tacynase-N, ones originating from bacteria such as Prolisin, Thermolysin, PS-protease and the like, Collagenase and Crotulus atrox protease and the like. Crude enzymes such as Thermoase and the like can also be used. An esterase-inhibitor such as a potato-inhibitor and the like can be used in combination when the crude enzyme has an esterase activity and the like due to impurities. It is necessary to carefully carried out the reaction not to take place side reactions due to ester hydrolysis reactions, when a thiol-proteinase such as papain or serine-proteinase such as trypsine is used because they are accompanied with the esterase activity.

The ZAPM formation reaction of this invention is to react ZA and PM in their thus prepared aqueous mixture solution under a pH condition under which the added proteolytic enzyme exerts the enzymatic activity. The reaction of this invention for the formation of the addition compound of ZAPM and PM is also pH-dependent in nature and therefore, the second step reaction of this invention can be carried out within a pH range of about 4 to about 9. However, it is most preferable to carry out it at a pH not more than 8 because the hydrolysis reaction of PM collaterally takes place at an alkalline side as the pH increases. Each one of ZA and PM which is used in this invention may be of the L-form or a mixture of the L-form and the D-form. Only the L-forms participate the peptide linkage formation reaction. The D-form of ZA when it also exists does not disturb the reaction. When PM is in a mixture of the L-form and D-form, ZAPM produced in the peptide linkage formation reaction forms ZAPM.PM preferentially with the D-form of PM to deposit out of the system. Accordingly, L-form PM should be at least in equimolar based on the L-form of ZA in the ZAPM formation reaction. However, it is necessary that the PM contains at least 1 mol of the L-form and is at least 2 mols in sum amount of the L- and D-form based on the molarity of L-form ZA, because ZAPM thus produced forms ZAPM.PM which is hardly soluble in water. Accordingly, it is desirable that the PM contains at least about 1 to about 5 mols of the L-form and is about 2 to about 5 mols in sum amount based on the molarity of the D-form ZA.

It is preferable in the process of this invention that concentrations of the substrates are as high as possible in the enzymatic reaction mixture, that is, an amount of the aqueous medium is as little as possible based on the amounts of the substrates as far as the reactions concern. However, an extremely small amount turns the reaction solution to a suspension state having a high viscosity at the end of the reaction which results in a difficulty in work-up of the reaction mixture. Accordingly, it is preferable that the amount of water is from 5 to 25 parts by weight in the reaction solution based on 1 part by weight of the L-form of ZA. Therefore, in order to meet with the range at the reaction, it is desirable to make a dilution in a case wherein the amount of water is less than the lower limit, or concentration in a case, wherein the amount of water exceeds the upper limit, of a mixture of both the substrates or solutions resulting from the respective production steps.

The amount of the enzyme is not limitative. The reaction completes in a shorter time when the used concentration is higher, while the reaction time becomes so much longer, when the concentrations is lower. However, it may be in a measure of 2 to 400 mg ($5 \times 10^{-5}$ to $1 \times 10^{-2}$ m M), preferably 5 to 100 mg ($1 \times 10^{-4}$ to $3 \times 10^{-2}$ m M) based on the amount by m mol of both the substrates. The reaction time depends on the reaction temperature and the used amount of the enzyme as the catalyst and can not be simply determined but is in a measure of 30 minutes to 50 hours in general.

The second step reaction of this invention is carried out at a temperature of about 10° C. to about 90° C., preferably from about 20° C. to about 50° C. in the view point of maintaining the enzymatic activity.

ZAPM.PM which is deposited can be easily recovered by a conventional means such as filtration, solvent extraction and the like. According to the process of this invention, the aqueous mixture solution prepared by mixing the aqueous solution of ZA and PM which have been obtained both in the first step reactions does not inhibit the enzymatic reaction of ZA and PM and the subsequent ZAPM.PM formation reaction. Then these reactions proceed in extremely smooth.

In the above-stated ZA production step, it is usually inevitable to take place the by-production of N-benzyloxycarbonyl-L-aspartyl-L-aspartic acid (hereinafter referred to as ZAA).

Generally, it seems unevitable that there takes place the by-production of N-benzyloxycarbonyl-L-aspartyl-L-aspartyl-L-phenylalanine methyl ester (hereinafter referred to as ZAAPM) in an amount which can not be negleted when ZA containing ZAA is reacted with PM in a process wherein no enzymatic reaction is utilized. Separation of ZAAPM from ZAPM is not easy and when it remains in the subsequent steps, it receives the Z removal to give L-aspartyl-L-aspartyl-L-phenylalanine methyl ester, which is also an extremely undersirable by-product because it is hardly separated from the object material, α-L-aspartyl-L-phenylalanine methyl ester. It has been predicted that ZAAPM or its addition compound with PM should also be produced as a by-product in an enzymatic reaction of ZA and PM when ZAA was coexist. Surprisingly, there is no substantial contamination due to ZAAPM or its addition compound with PM in the obtained ZAPM.PM in the process of this invention. According to the process of this invention, it is possible to greatly reduce the number of steps as a whole because it is not necessary to isolate ZA and PM, and as a result, it is possible to prevent the loss of raw materials, intermediates and the like in the omitted steps. As phenylalanine and aspartic acid remaining unreacted in the reactions of N-benzyloxycarbonylation and esterification can be recovered together with PM and ZA remaining unreacted in the condensation step and further together with phenylalanine, which may be possibly produced as a by-product in a side reaction, wherein PM is hydrolyzed, from a residual solution, from which ZAPM.PM produced in the condensation step has been separated, the loss of raw materials are small in the process of this invention.

Furthermore, as the base and acid which are used both in the first step reactions can be effectively utilized to neutralize each other, it is possible to reduce the used amounts of the base and acid.

DESCRIPTION OF THE PREFERRED EMBODIMENTS

This invention is further explained in detail in the following Examples.

EXAMPLE 1

Preparation of an Aqueous ZA Solution

Into 360 ml of water were suspended 319.4 g (2.4 mols) of L-aspartic acid and 480 ml (4.8 mols) of a 10 N aqueous solution of sodium hydroxide was added to completely dissolve it. Into the resulting solution 480 g of benyloxycarbonyl chloride (purity 93%, 2.62 mols) and 330 ml (3.3 mols) of a 10 N aqueous solution of sodium hydroxide were simultaneously added dropwise under vigorous stirring in a temperature range between 0° and 12° C. and a pH range between 9.5 and 12.0 during a course of 6 hours. After the completion of the addition, it was further stirred at room temperature for about 2 hours, and then 1 liter of toluene was added followed by the separation of the aqueous phase and the toluene phase. The aqueous phase was 2185.5 g in total amount and it was recognized that ZA was produced in an amount of 607.0 g (yield: 94.7%) from the high speed liquid chromatography analysis. ZAA is also produced as a by-product in an amount of 22.9 g.

Preparation of an Aqueous PM Solution 991.5 g Of DL-phenylalanine (6 mols) were added into 3320 g of methanol containing 437.4 g (12.0 mols) of hydrogen chloride and heated to reflux in an oil bath for 3 hours. It was recognized from the analysis of the Volhard method that chlorine ions existed in an amount of 9.23 mols. After 1 liter of distilled water and 259.0 g (3.22 mols) of a 48% aqueous solution of sodium hydroxide were added into the solution to neutralize hydrogen chloride which was excess based on the charged phenylalanine, methanol was completely removed by distillation in a rotary evaporator while 1.5 liters of distilled water were added. The total amount of the concentrated solution was 2821.0 g and it was recognized that DL-phenylalanine methyl ester (DL-PM) was produced in an amount of 1007.1 g (yield: 93.7%) from the high speed chromatography analysis.

Preparation of ZAPM.PM by the Reaction of ZA and PM 192.43 g Of the thus prepared ZA aqueous solution (containing 0.2 mol of ZA) and 250.98 g of the DL-PM aqueous solution (containing 0.5 mol of DL-PM) were admixed. After 265 ml of distilled water was added, pH of the mixture was adjusted to 6.3 by a 5 N aqueous solution of sodium hydroxide. Into this solution 7.2 g of thermoase ($1.6 \times 10^6$ PU/g, made by Daiwa Kasei) and 1.3 g of calcium acetate monohydrate were added and the reaction carried out at 40° C. under stirring. After 8 hours, the produced suspension was filtered through a glass filter and crystalls were washed with 500 ml of cold water.

This crystalls were of an addition compound of N-benzyloxycarbonyl-α-L-aspartyl-L-phenylalanine methyl ester and mainly D-form of phenylalanine methyl ester (Z-APM.D-PM). The yield was found 85.6% from the high speed liquid chromatography analysis. It was confirmed that these crystalls were of an one to one addition compound of Z-APM and mainly D-form of PM from the facts that NMR and IR spectra, elemental analysis data and the specific rotation of the crystalls obtained in a recrystallization from a mixture solvent of ethyl acetate and n-hexane substantially coincide with the data disclosed in U.S. Pat. No. 4,165,311.

No ZAAPM nor its PM addition compound was detected.

EXAMPLE 2

Preparation of an Aqueous PM solution

Into 25 g of the aqueous solution containing DL-PM, which was obtined in Preparation of an Aqueous PM Solution in Example 1, added 50 ml of methyl isobutylketone and 6 ml of a 10 N aqueous solution of sodium hydroxide was added dropwise, while both the liquids were stirred to mix. After the stirring was stopped, the formed two phases were separated. Into the methyl isobutylketone phase were added 6 g of a concentrated hydrochloric acid and 15 ml of water to stir for mixing. After the stirring was stopped, the formed two phase were separated to give 30 g of the aqueous phase. It was confirmed that 8.3 g of DL-PM was contained in the aqueous phase from the high speed liquid chromatography.

Preparation of ZAPM.PM by the Reaction ZA and PM 3.240 g Of the thus obtained aqueous solution of DL-PM (containing 5 m mols of DL-PM) were admixed with 1.924 g of the aqueous ZA solution (containing 2 m mols of ZA) obtained in Preparation of an Aqueous ZA Solution in Example 1, 0.6 ml of 1 N aqueous solution of sodium hydroxide and 2 ml of distilled water, when the pH was 6.2. Into this mixture were added 50 mg of Thermolysin and 5 mg of calcium acetate monohydrate and the reaction was carried out in an incubator at 40° C. for 8 hours. The reaction mixture was filtered and the remaining crystalls were recovered after they were washed with 10 ml of cold water to obtain an addition compound of Z-APM and mainly D-form of PM (Yield from the high speed liquid chromatography was 86.2%). No ZAAPM nor its PM addition compound was detected.

EXAMPLE 3

Preparation of an Aqueous PM Solution

A mixture of 198.23 g (1.2 mols) of L-phenylalanine, 87.48 g (2.4 mols) of hydrogen chloride and 576 g of methanol was heated to reflux for 3 hours. After cooling, chlorine ions were found to exist there in an amount of 1.893 mols from the analysis of the reaction mixture by the Volhard method. Into the solution 200 ml of distilled water was added and further 40.48 g (0.693 mol) of 48% aqueous solution of sodium hydroxide was added to neutralized hydrogen chloride which was excess based on the charged phenylalanine. Methanol was completely removed from the reaction mixture by distillation in an rotary evaporator, while 300 ml of distilled water was added. The total amount of the concentrated solution was 543.9 g and it was recognized that L-phenylalanine methyl ester (L-PM) was produced in an amount of 206.6 g (yield: 96.1%) from the high speed liquid chromatography analysis.

Preparation of ZAPM.PM by the Reaction of ZA and PM 179.45 g Of the thus prepared L-PM aqueous solution (containing 0.4 mol of L-PM) were admixed with 192.43 g of the aqueous ZA solution (containing 0.2 mol of ZA) obtained in Preparation of an Aqueous ZA Solution in Example 1 and further pH of the resulting solution was adjusted to 5.75 by 1 N-HCl after addition of 240 ml of distilled water. Into this solution, 7.2 g of Thermoase PS-160 and 1.3 g of calcium acetate monohydrate were added and the reaction was carried out with stirring. After 10 hours, the reaction was stopped and the work-up as well as the analysis were carried out in the same way as in Example 1. NMR and IR spectra, elemental analysis data and the specific rotation substantially coincide with those of the addition compound of N-benzyloxycarbonyl-α-L-aspartyl-L-phenylalanine methyl ester and L-phenylalanine methyl ester (ZAPM.L-PM) which were disclosed in U.S. Pat. No. 4,165,311. The yield of ZAPM.L-PM was 83.2%. No ZAAPM nor its addition compound with PM was detected.

EXAMPLE 4

Preparation of an Aqueous ZA Solution

Into a mixture wherein 53.24 g (0.4 mol) of L-aspartic acid and 70.26 g (0.663 mol) of sodium carbonate were suspended in 165 g of water, 80 g benzyloxycarbonyl chloride (purity 93%, 0.436 mol) was added dropwise under vigorous stirring during the course of 6 hours, in a temperature range of 0° to 12° C. After the stirring was further continued over night at room temperature, 200 ml of toluene was added to the reaction mixture to mix and stir and the aqueous phase and the toluene phase were separated. The total amount of the aqueous phase was 325 g and it was recognized that ZA was produced there in an amount of 97.3 g (yield: 91.0%) from the high speed liquid chromatography analysis. There was also produced 4.6 g of ZAA as a by-product.

Preparation of ZAPM.PM by the Reaction of ZA and PM 178.52 Of the thus prepared aqueous ZA solution (containing 0.2 mol of ZA) and 250.98 g of the aqueous DL-PM solution (containing 0.5 mol of DL-PM) which was obtained in Preparation of an Aqeuous PM Solution in Example 1 were admixed and pH of the resulting solution was adjusted to 6.11 by a 5 N aqueous solution of sodium hydroxide after 280 ml of distilled water was added. Into this mixture 7.2 g of Thermoase PS-160 and 1.3 g of calcium acetate monohydrate were added and the reaction was carried out under stirring at 40° C. for 10 hours. The work-up was carried out in the same way as in Example 1 and an addition compound of ZAPM and mainly D-form of PM was obtained. The yield was 83.3%. No ZAAPM not its addition compound with PM was detected.

EXAMPLE 5

Preparation of an Aqueous ZA Solution

Into a mixture wherein 31.94 g (0.24 mol) of L-aspartic acid was dissolved in 96 ml (0.48 mol) of a 5 N aqueous solution of potassium hydroxide, 48 g of benzyloxycarbonyl chloride purity: 93%, 0.262 mol) and 66 ml (0.33 mol) of a 5 N aqueous solution of potassium hydroxide were simultaneously added dropwise in a temperature range between 0° and 12° C. and in a pH range between 9.5 and 12.0 under vigorous stirring in the course of 6 hours. After the completion of the addition, it was stirred at room temperature for 2 hours. After that, 200 ml of toluene was added to admix and the resulting mixture was stirred. Then the aqueous phase and the toluene phase were separated. It was recognized from the high speed liquid chromatography analysis that ZA was produced in the aqueous solution in an amount of 58.4 g (yield: 91.0%). ZAA was also produced in an amount of 3.2 g.

Preparation of ZAPM.PM by the Reaction of ZA and PM 237.19 g Of the thus prepared aqueous ZA solution (containing 0.2 mol of ZA) and 250.98 g of the aqueous DL-PM solution (containing 0.5 mol of DL-PM) prepared in Preparation of an Aqueous PM Solution in Example 1 were admixed and after 350 ml of distilled water was added, the pH of the resulting mixture was adjusted to 6.3 by a 5 N aqueous solution of potassium hydroxide. Into the mixture 4.8 g of Termoase PS-160 and 0.8 g of calcium acetate monohydrate was added. Then, the reaction was carried out at 40° C. for 18 hours. The work-up was carried out in the same way as in Example 1 and the addition compound of ZAPM and mainly D-PM was obtained. The yield was 83.5%. No ZAAPM nor its PM addition compound was detected.

EXAMPLE 6

Preparation of an Aqueous PM Solution

Into a mixture liquor of 99.1 g (0.6 mol) of DL-phenylalanine and 288 g of methanol was added 115.4 g of concentrated sulfuric acid and it was heated to reflux in an oil bath for 3 hours. After cooling 100 ml of distilled water and 53.1 ml of a 48% aqueous solution of sodium hydroxide were added into the reaction mixture. After that, methanol was removed from the reaction mixture by distillation in an rotary evaporator, while 100 ml of distilled water was added. This gave a concentrated solution in an amount of 411.1 g and it was recognized from the high speed liquid chromatography analysis that DL-PM was produced in an amount of 101.6 g (yield: 94.5%).

Production of ZAPM.PM by the Reaction of ZA and PM 181.26 g Of the thus prepared adqueous DL-PM solution (containing 0.25 mol of DL-PM) was admixed with 96.68 g of the aqueous ZA solution obtained in Preparation of an Aqueous ZA Solution in Example 1. Furthermore, after 24 ml of distilled water was added, pH of the resulting mixture was adjusted to 6.3 by a 5 N aqueous solution of sodium hydroxide.

Into this mixture 3 g of Thermoase and 0.65 g of calcium acetate monohydrate were added and the reaction was carried out at 40° C. for 12 hours under stirring. The work-up was carried out in the same way as in Example 1 and an addition compound of ZAPM and mainly D-form of PM was obtained. The yield was 84.9%. No ZAAPM nor its PM addition compound was detected.

We claim:

1. A process for producing an addition compound of a dipeptide ester and an amino acid ester comprising reacting aspartic acid and benzyloxycarbonyl chloride in an aqueous solution in the presence of a base to prepare a solution containing N-benzyloxycarbonyl aspartic acid, reacting separatedly phenylalanine with methanol in the presence of an acid to produce phenylalanine methyl ester, substituting excess methanol with water to convert it to an aqueous solution of phenylalanine methyl ester, admixing it with the above-prepared aqueous solution containing N-benzyloxycarbonyl aspartic acid, adding a proteolytic enzyme into the resulting mixture liquor under conditions, under which no substantial deactivation of the enzyme occurs, reacting N-benzyloxycarbonyl aspartic acid with phenylalanine methyl ester to deposit an addition compound of N-benzyloxycarbonyl-α-L-aspartyl-L-phenylalanine methyl ester and phenylalanine methyl ester and recovering the addition compound.

2. The process as set forth in claim 1, wherein aspartic acid and phenylalanine methyl ester are respectively used in the form of L-forms or a mixture of L-form and D-form to recover the addition compound of N-benzyloxycarbonyl-α-L-aspartyl-L-phenylalanine methyl ester and L- or D-phenylalanine methyl ester or a phenylalanine methyl ester being in a mixture form of both the configurations.

3. The process as set forth in claim 2, wherein a metalloproteinase is used as the proteolytic enzyme.

4. The process as set forth in claim 3, wherein the amount ratio of phenylalanine methyl ester to N-benzyloxycarbonylaspartic acid at the time of the enzymatic reaction is at least about 1 by mol of the L-form of the former and from about 2 to about 5 by mol of the sum amount of the L-form and the D-form thereof based on the molarity of the later.

5. The process as set forth in claim 4, wherein a hydroxide, carbonate or a hydrogen carbonate of an alkali metal is used as the base and an inorganic strong acid is used as the acid.

6. The process as set forth in any claim of claims 1 to 5, wherein after aspartic acid and benzyloxycarbonyl chloride are reacted in the aqueous solution in the presence of the base, the reaction liquor is washed with an organic solvent which is capable of forming binary phases with water, to prepare the aqueous solution containing N-benzyloxycarbonylaspartic acid.

7. A process for producing an addition compound of a dipeptide ester and an amino acid ester comprising reacting aspartic acid and benzyloxycarbonyl chloride in an aqueous solution in the presence of a base to prepare a solution containing N-benzyloxycarbonylaspartic acid, reacting separatedly phenylalanine with methanol in the presence of an acid to produce phenylalanine methyl ester adding a base therein to liberate the phenylalanine methyl ester, adding to admix an organic solvent capable of forming binary phases with water to extract the phenylalanine methyl ester in the organic solvent phase, separating the phases, adding an acidic aqueous solution into the organic solvent phase to admix and contact with to back-extract the phenylalanine methyl ester into the aqueous phase, separated the phases, admixing the aqueous phase with the above prepared aqueous solution containing N-benzyloxycarbonyl-aspartic acid, adding a proteolytic enzyme into the resulting mixture liquor under conditions under which no substantial deactivation of the enzyme occurrs, reacting N-benzyloxycarbonylaspartic acid with phenylalanine methyl ester to deposit an addition compound of N-benzyloxycarbonyl-α-L-aspartly-L-phenylalanine methyl ester and phenylalanine methyl ester and recovering the addition compound.

8. The process as set forth in claim 7, wherein aspartic acid and phenylalanine methyl ester are respectively used in the form of L-forms or a mixture of L-form and D-form to recover the addition compound of N-benzyloxycarbonyl-α-L-aspartyl-L-phenylalanine methyl ester and L- or D-phenylalanine methyl ester or a phenylalanine methyl ester being in a mixture form of both the configurations.

9. The process as set forth in claim 8, wherein a metalloproteinase is used as the proteolytic enzyme.

10. The process as set forth in claim 9, wherein the amount ratio of phenylalanine methyl ester to N-benzyloxycarbonylaspartic acid at the time of the enzymatic reaction is at least about 1 by mol of the L-form of the former and from about 2 to about 5 by mol of the sum amount of the L-form and the D-form thereof based on the molarity of the later.

11. The process as set forth in claim 10, wherein a hydroxide, carbonate or a hydrogen carbonate of an alkali metal is used as the based and an inorganic strong acid is used as the acid.

12. The process as set forth in any claim of claims 7 to 11, wherein after aspartic acid and benzyloxycarbonyl chloride are reacted in the aqueous solution in the presence of the base, the reaction solution is washed with an organic solvent which is capable of forming binary phases with water, to prepare the aqueous solution containing N-benzyloxycarbonylaspartic acid.

* * * * *

UNITED STATES PATENT AND TRADEMARK OFFICE
CERTIFICATE OF CORRECTION

PATENT NO. : 4,521,514

DATED : June 4, 1985

INVENTOR(S) : Oyama, Kiyotaka; Irino, Shigeaki; Harada, Tsuneo; Nakamura, Masao

It is certified that error appears in the above-identified patent and that said Letters Patent is hereby corrected as shown below:

Column 1, line 26, delete "imported" and insert therefor: --important--.

Column 4, line 47, delete "D-form ZA" and insert therefor: --L-form ZA--.

Signed and Sealed this

Eleventh Day of February 1986

[SEAL]

Attest:

DONALD J. QUIGG

Attesting Officer

Commissioner of Patents and Trademarks